(12) United States Patent
Benghezal et al.

(10) Patent No.: US 8,790,909 B2
(45) Date of Patent: Jul. 29, 2014

(54) **STRAINS OF *HELICOBACTER PYLORI* AND USES THEREOF**

(75) Inventors: Mohammed Benghezal, Scarborough (AU); Alma Fulurija, White Gum Valley (AU); Wei Lu, Nedlands (AU); Hans-Olof Nilsson, Subiaco (AU); Barry J. Marshall, Subiaco (AU)

(73) Assignee: Ondek Pty. Ltd., Perth (AU)

( * ) Notice: Subject to any disclaimer, the term of this patent is extended or adjusted under 35 U.S.C. 154(b) by 0 days.

(21) Appl. No.: 13/376,377

(22) PCT Filed: Jun. 3, 2010

(86) PCT No.: PCT/AU2010/000689
§ 371 (c)(1),
(2), (4) Date: Feb. 17, 2012

(87) PCT Pub. No.: WO2010/139018
PCT Pub. Date: Dec. 9, 2010

(65) Prior Publication Data
US 2012/0144509 A1    Jun. 7, 2012

(30) Foreign Application Priority Data
Jun. 3, 2009    (AU) ................................ 2009902545

(51) Int. Cl.
*C12N 1/00*    (2006.01)

(52) U.S. Cl.
USPC ..................................................... 435/252.1

(58) Field of Classification Search
None
See application file for complete search history.

(56) References Cited

U.S. PATENT DOCUMENTS

2007/0134264 A1    6/2007    Marshall

FOREIGN PATENT DOCUMENTS

WO    02/07763    1/2002

OTHER PUBLICATIONS

Sicinschi et al. (J. Microbiol. Methods, 55:625-633, 2003).*
Guo et al. "Rapid genetic analysis of Helicobacter pylori gastric mucosal colonization in suckling mice", PNAS 99(12):8654-8359, 2002.
Guo et al. "Helicobacter pylori mutagenesis by mariner in vitro transposition", FEMS Immunology and Medical Microbiology 30:87-93, 2000.
Ge et al. "Fumarate reductase is essential for Helicobacter pylori colonization of the mouse stomach", Microbial Pathogenesis 29:279-287, 2000.
Yamoka et al. "Helicobacter pylori Infection in Mice: Role of Outer Membrane Proteins in Colonization and Inflammation", Gastroenterology 123:1992-2004, 2002.
International Search Report and Written Opinion; PCT/AU2010/000689; Aug. 24, 2010; 13 pages.
International Preliminary Report on Patentability; PCT/AU2010/000689; Dec. 6, 2011; 9 pages.
Ladeira, et al.; "Relationship among oxidative DNA damage, gastric, ucosal density and the relevance of cagA, vacA and iceA genotypes of Hilicobacter pylori" ;Dig Dis Sci, 2008; vol. 53, pp. 248-255.
Blaser; "Role of vaca and the caga locus of helicobacter pylori in human disease"; Alimentary Pharmacology & Therapeutics; 1996; vol. 10, no. suppl. 01; pp. 73-77.

* cited by examiner

*Primary Examiner* — Brian J Gangle
(74) *Attorney, Agent, or Firm* — Pepper Hamilton LLP

(57) ABSTRACT

The present invention relates to strains of *Helicobacter pylori* useful for the delivery of biologically active agents. In particular, the present invention provides an isolated strain of *H. pylori* having: (a) low pathogenicity; (b) ability to naturally transform; and (c) ability to colonise mouse stomach mucosa without host adaptation.

12 Claims, 12 Drawing Sheets

| Strain | Transformation | Strain | Transformation | Strain | Transformation |
|---|---|---|---|---|---|
| K1 | ++ | H21 | ++ | H44 | + |
| K2 | - | H22 | - | H45 | - |
| K3 | - | H23 | + | H51 | + |
| K4 | +++ | H24 | + | H52 | + |
| K5 | - | H25 | ++++ | H53 | + |
| K6 | +++ | H26 | + | H54 | + |
| K7 | - | H27 | ++++ | H55 | +++ |
| K8 | + | H28 | - | H66 | + |
| K9 | + | H29 | ++++ | H67 | + |
| K10 | +++ | H30 | - | H68 | + |
| K11 | +++ | H31 | + | H69 | ++++ |
| K12 | +++ | H32 | - | H70 | + |
| K13 | - | H33 | + | | |
| K14 | + | H34 | ++ | | |
| K15 | - | H35 | - | | |
| K16 | ++++ | H36 | ++++ | | |
| K17 | ++ | H37 | + | | |
| K18 | ++ | H38 | ++ | | |
| K19 | ++ | H39 | +++ | | |
| K20 | - | H40 | ++ | | |
| K21 | ++ | H41 | + | | |
| K22 | ND | H42 | ++ | | |
| K23 | - | H43 | | | |

Frequency (%) 57.53

FIGURE 1

| Strain | Transformation | Colonisation | Strain | Transformation | Colonisation | Strain | Transformation | Colonisation |
|---|---|---|---|---|---|---|---|---|
| K1 | ++ | - | H21 | ++ | - | H44 | + | - |
| K4 | +++ | - | H23 | + | - | H51 | + | ++ |
| K6 | +++ | + | H24 | + | - | H52 | + | +++ |
| K8 | + | + | H25 | +++ | ++ | H53 | + | - |
| K9 | + | - | H26 | + | - | H54 | + | +++ |
| K10 | +++ | - | H27 | +++ | ++ | H55 | +++ | - |
| K11 | +++ | ++ | H29 | ++++ | - | H66 | + | - |
| K12 | +++ | - | H32 | + | - | H67 | + | - |
| K14 | + | - | H34 | + | - | H68 | + | + |
| K16 | ++++ | + | H35 | ++++ | + | H69 | ++++ | ++ |
| K17 | ++ | - | H37 | + | + | H70 | + | - |
| K18 | + | - | H38 | ++ | + | | | |
| K19 | ++ | | H39 | +++ | ++ | | | |
| K21 | ++ | | H40 | ++ | - | | | |
| | | | H41 | + | | | | |
| | | | H42 | ++ | | | | |
| | | | H43 | | | | | |

FIGURE 2

| Strain | Round 1 | Round 2 | Round 3 | Average % |
|---|---|---|---|---|
| | No. Colonised Animals | | | |
| K6 | 5/10 | 7/11 | 7/10 | 61.2 |
| K8 | 5/10 | 9/12 | 6/10 | 61.7 |
| K11 | 1/10 | 4/12 | 1/10 | 17.7 |
| K18 | 6/10 | 3/10 | 8/10 | 56.7 |
| H51 | 4/10 | 0/10 | - | 20 |
| H52 | 0 | 1/10 | - | 5 |
| H54 | 0 | 0 | - | 0 |
| H68 | 4/12 | 0 | - | 16.7 |
| H69 | 1/10 | 7/10 | - | 40 |
| H27 | 8/10 | 1/10 | - | 45 |
| H37 | 3/10 | 2/10 | - | 25 |
| H39 | 0/10 | 0 | - | 0 |
| H40 | 7/10 | 8/10 | - | 75 |
| H41 | 8/10 | 0 | - | 40 |
| H25 | 4/10 | 0 | - | 20 |

FIGURE 3

| Strain | No Animals Colonised | % |
|--------|----------------------|------|
| K6     | 4/6                  | 66.6 |
| K8     | 3/6                  | 50   |
| K11    | 0                    | 0    |
| K18    | 2/4                  | 50   |
| H27    | 3/6                  | 50   |
| H41    | 0                    | 0    |

FIGURE 4

| Strain | No. animals colonised | % |
|---|---|---|
| K4 | 3/3 | 100 |
| K12 | 1/3 | 33 |
| K8 | 1/3 | 33 |

FIGURE 7

| Protein | | CagA | CagA-Ptyr | CagY | VacA | OipA | BabA | SabA | UreB | IL-8 | Mouse | Gerbil | Monkey |
|---|---|---|---|---|---|---|---|---|---|---|---|---|---|
| Size | | 140 kD | 140 kD | 220 kD | 80 kD | 34 kD | 74 kD | 60 kD | 65 kD | | | Colonisation | |
| Isolates | | | | | | | | | | | | | |
| OND737 | K6 | 70kD * | neg | pos | pos | pos (50kD) | pos | pos (70 kD) | pos | neg | Log 3 | no | yes |
| OND738 | K8 | 60kD * | neg | neg | neg | neg | neg | neg | pos | neg | Log 3 | no | no |
| OND739 | K11 | pos | pos | pos | pos | pos | pos (80 kD) | pos (70 kD) | pos | pos | Log 2 | no | yes |
| OND740 | K18 | 60, 70kD * | neg | pos (170kD) | neg | pos | neg | neg | nd | neg | Log 3 | no | tbd |
| OND256 | K12 | pos | pos | nd | neg | neg | neg | pos | nd | pos | Log 4 | yes | tbd |
| OND248 | K4 | pos | pos | nd | neg | neg | pos | pos | nd | pos | Log 4 | yes | tbd |

\* truncated form, non-functional
tbd to be determined
nd not determined pos positive
neg negative

| Isolates | | Transformability | Age | Sex | Atrophy | Cell infiltration | | Hp |
|---|---|---|---|---|---|---|---|---|
| | | | | | | Lymphocyte | Granulocyte | |
| OND737 | K6 | +++ | 58 | f | 1 | 1 | 1 | 1 |
| OND738 | K8 | + | 57 | f | 0 | 2 | 1 | 1 |
| OND739 | K11 | +++ | 63 | f | 0 | 1 | 1 | 3 |
| OND740 | K18 | + | 52 | f | 1 | 2 | 3 | 1 |
| OND256 | K12 | +++ | 56 | f | 0 | 2 | 1 | 1 |
| OND248 | K4 | +++ | 64 | m | 0 | 1 | 1 | 3 |

0 = no
1 = yes, slight
2 = yes, moderate
3 = yes, high grade

FIGURE 9

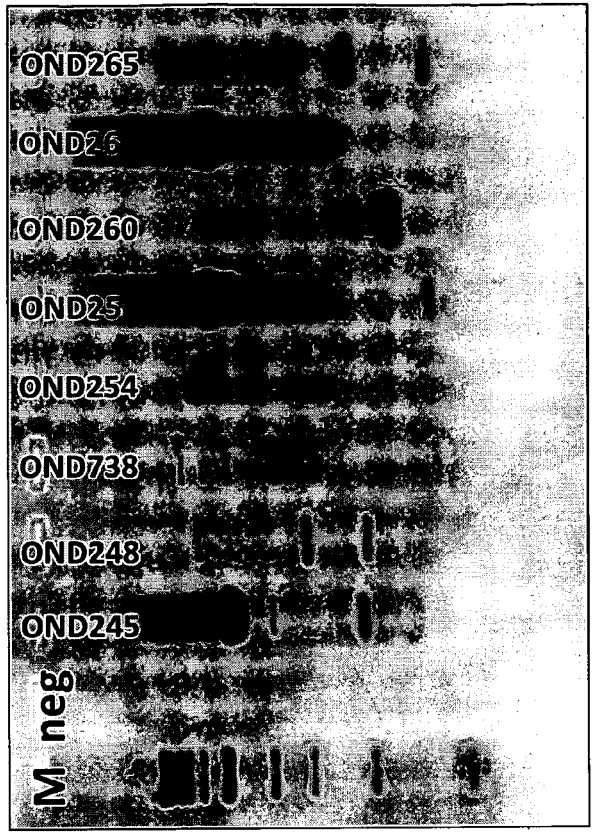
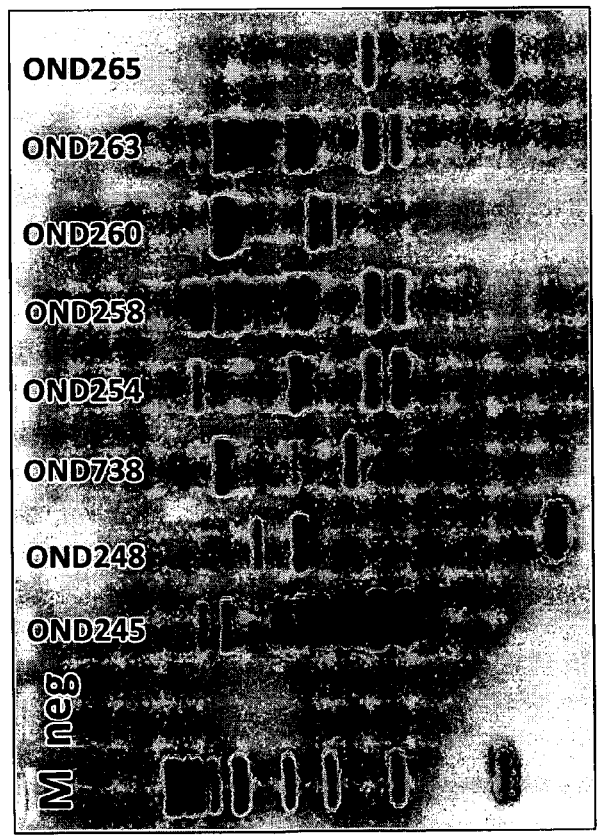
FIGURE 11

SEQUENCE LISTING

```
<160> NUMBER OF SEQ ID NOS: 2

<210> SEQ ID NO 1
<211> LENGTH: 10
<212> TYPE: DNA
<213> ORGANISM: Helicobacter pylori

<400> SEQUENCE: 1
ccgcagccaa                                                        10

<210> SEQ ID NO 2
<211> LENGTH: 10
<212> TYPE: DNA
<213> ORGANISM: Helicobacter pylori

<400> SEQUENCE: 2
aacgcgcaac                                                        10
```

STRAINS OF *HELICOBACTER PYLORI* AND USES THEREOF

FIELD

RELATED APPLICATIONS

This application is the U.S. national stage under 35 USC §371 of International Application Number PCT/AU2010/000689, filed on 3 Jun. 2010, which claims priority to Australian Application No. 2009902545, filed on 3 Jun. 2009. The contents of each of these applications are hereby incorporated by reference in their entireties.

The present invention relates to strains of *Helicobacter pylori* useful for the delivery of biologically active agents.

BACKGROUND

Live bacteria, such as probiotic bacteria or live attenuated pathogens, represent attractive vehicles for the delivery of a range of biologically active agents such as vaccine antigens, biologically active molecules or even DNA. The advantages inherent in bacterial delivery vehicles include oral administration and the sustained release of the compound over a protracted period of time, eliminating the need for repeat doses.

Current commercially available vaccines and medications are largely parenterally administered, require multiple doses and depend on medical staff and a cold chain. Live bacterial vehicles offer an alternative to conventional prophylactic and therapeutic agents in that they can be delivered orally, may only require a single dose and are able to deliver large molecules, for example, multiple antigens. In addition, bacterial vehicles are well suited to large-scale manufacture and formulation and are stable when lyophilised. These attributes make this form of delivery attractive and could result in increased compliance, greater distribution and reduced cost for a variety of vaccines and medications.

Several bacterial delivery systems have been proposed based on various bacteria including *Shigella* spp. (U.S. Pat. No. 7,235,234), *Salmonella* spp. (US Patent Application No. 20090022691) and *Lactobacillus* spp. (US Patent Application No. 20090074734), but there are a number of problems inherent in these systems.

In general, bacteria are manipulated to produce strains with the required characteristics for use as delivery vehicles. Importantly, the safety profile of the bacteria should be ensured. Traditionally bacteria for use as delivery vehicles have been attenuated to be less pathogenic or non-pathogenic; however, it is difficult to ensure the safety of these bacteria as virulence genes can be reacquired and result in the bacteria reverting to a virulent form with the ability to cause disease. Further, manipulating bacterial strains to be amenable to transformation or to colonise an animal model may result in the production of secondary undesirable characteristics, or at the very least hinder experimentation and delay transition of bacterial delivery vehicles into the clinic. For example, manipulation of a strain such that experiments can be performed in an animal model such as a mouse, may result in the strain not colonising the target host, typically humans. Accordingly, manipulating bacteria in order produce a strain with desired characteristics should be avoided where possible.

The inventors of the present invention have previously proposed the use of *Helicobacter pylori* in a bacterial delivery system (US Patent Application No. 20070134264), which solved a number of the problems identified above; however, while US Patent Application No. 2007013464 provides a wealth of information regarding the use of *H. pylori* as a bacterial delivery vehicle, the development of specific bacterial strains with specific characteristics would be useful.

SUMMARY

In a first aspect, the present invention provides an isolated strain of *H. pylori* having the following characteristics: (a) low pathogenicity; (b) ability to naturally transform; and (c) ability to colonise mouse stomach mucosa without host adaptation.

*H. pylori* have unique characteristics that make it suitable for use as a live bacterial delivery vehicle for biologically active agents. The *H. pylori* strains of the present invention are isolated from individuals that are asymptomatic and show minimal pathology, rendering the strains safe for use in humans. Further, the strains of the present invention are naturally transformable and are able to colonise the *H. pylori*-mouse model without prior adaptation. This facilitates preclinical experimentation and means that manipulation to the strains is minimal, allowing accurate, direct translation of the results to humans. Accordingly, the *H. pylori* strains of the present invention are highly suitable for use as live bacterial delivery vehicles.

In some embodiments, the *H. pylori* of the present invention are able to form a chronic infection in a mammalian subject.

In some embodiments, the *H. pylori* strains of the present invention do not express one or more functional virulence factors, for example vacA s1 or cagA.

In a second aspect, the present invention provides an isolated strain of *H. pylori* which is either:
  (i) vacA s1 or cagA negative; or
  (ii) vacA s2 and cagA positive;
wherein said strain of *H. pylori* has
  (a) low pathogenicity,
  (b) ability to naturally transform; and
  (c) ability to colonise mouse stomach mucosa without host adaptation.

In some embodiments, the present invention provides strains of *H. pylori* having the characteristics of a strain selected from the group consisting of OND737, as deposited in the National Measurement Institute under Accession No. V09/009,101; OND738, as deposited in the National Measurement Institute under Accession No. V09/009,102; OND739, as deposited in the National Measurement Institute under Accession No. V09/009,103; OND248, as deposited in the National Measurement Institute under Accession No. V10/014,059; OND256 as deposited in the National Measurement Institute under Accession No. V10/014,060 and OND740, as deposited in the National Measurement Institute under Accession No. V09/009,104, or a mutant or derivative thereof having the abilities as defined described above.

In a third aspect, the present invention provides *H. pylori* strain OND737, as deposited in the National Measurement Institute under Accession No. V09/009,101.

In a fourth aspect, the present invention provides *H. pylori* strain OND738, as deposited in the National Measurement Institute under Accession No. V09/009102.

In a fifth aspect, the present invention provides *H. pylori* strain OND739, as deposited in the National Measurement Institute under Accession No. V09/009,103.

In a sixth aspect, the present invention relates to the *H. pylori* strain OND740, as deposited in the National Measurement Institute under Accession No. V09/009,104.

In a seventh aspect, the present invention relates to the *H. pylori* strain OND248, as deposited in the National Measurement Institute under Accession No. V10/014,059.

In an eighth aspect, the present invention relates to the *H. pylori* strain OND256, as deposited in the National Measurement Institute under Accession No. V10/014,060.

The isolated *H. pylori* strain may be transformed to produce a recombinant strain that expresses a gene of interest. In some embodiments, the gene of interest is encoded by a nucleic acid, which is preferably obtained in an isolated form. It will be appreciated by those skilled in the art that the isolated nucleic acid molecule of the present invention may be cDNA, genomic DNA, RNA, or a hybrid molecule thereof. Preferably, the isolated nucleic acid is cDNA.

Preferably the isolated nucleic acid is integrated into the genome of the recombinant strain.

The isolated nucleic acid may encode a polypeptide homologous or heterologous to *H. pylori*.

In some aspects, the isolated nucleic acid encodes a biologically active agent such as an antigen, an organic molecule, a pharmacological agent eg a therapeutic agent or prophylactic agent, such as a gene product or gene sequence (isolated nucleic acid).

The natural features of *H. pylori* infection such as the presence of specific, non-protective circulating antibodies and life-long persistence mean that *H. pylori* is particularly useful in delivering vaccine antigens. Accordingly, in some embodiments, the present invention provides a method of inducing an antibody response in an individual by administering a recombinant strain of *H. pylori*, which expresses an antigen of interest.

In a ninth aspect, the present invention provides a method of identifying a strain of *H. pylori* suitable for delivering biologically active agents in vivo, comprising: (a) isolating a *H. pylori* strain from an individual asymptomatic for *H. pylori* infection; (b) determining whether the strain has the ability to naturally transform; and (c) determining whether the strain has the ability to colonise mouse stomach mucosa without host adaptation, wherein strains with the ability to naturally transform and colonise mouse stomach mucosa without host adaptation are suitable for delivering biologically active agents in vivo.

In an eleventh aspect, the present invention provides an optimised animal model of *Helicobacter* infection, wherein animals are feed casein-rich food and/or acidified water such that colonization by *Helicobacter* species is enhanced relative to animals not feed with casein-rich food and/or acidified water.

In some embodiments, the animals are feed both casein-rich food and acidified water, wherein the water is about pH2. In some embodiments, the animals are mice.

In a twelfth aspect, the present invention provides use of randomly amplified polymorphic DNA polymerase chain reaction for the identification of *Helicobacter* species.

In some embodiments, *Helicobacter* DNA is amplified by polymerase chain reaction using a forward primer having the sequence shown in SEQ ID NO:1 and a reverse primer having the sequence shown in SEQ ID NO:2.

BRIEF DESCRIPTION OF THE FIGURES

FIG. 1: *H. pylori* clinical isolates were tested for natural transformation. 14 strains from the Karolinska (K) Institute and 28 strains from SCGH (H) were identified as being transformable with DNA, based on their antibiotic resistance phenotype. Transformable strains are indicated by the number of transformant colonies obtained on selective plates: + low (<20), ++ (20-50), +++ (>50), ++++ (>100).

FIG. 2: Transformable *H. pylori* strains were tested in the DBA/2 mouse model for colonisation of the stomach. Mice (n=3) were challenged with $1\times10^9$ CFU/ml bacteria. 4 weeks later bacteria were cultured from mouse stomach tissue and quantitated. Colonisation level was graded according to the number of colonies obtained: + low (<20), ++ (20-50), +++ (>50), ++++ (>100).

FIG. 3: Transformable *H. pylori* strains were tested in the DBA/2 mouse model for colonisation of the stomach. Mice (n=10-12) were challenged with $1\times10^9$ CFU/ml bacteria. 4 weeks later bacteria were cultured from mouse stomach tissue and quantitated. Colonisation frequency was determined by the number of mice infected with *H. pylori* per group. Results are expressed as individual and average percent colonisation per group.

FIG. 4: *H. pylori* strains were tested in the DBA/2 mouse model for long term colonisation of the stomach. Mice (n=4-6) were challenged with $1\times10^9$ CFU/ml bacteria. 6 months later bacteria were cultured from mouse stomach tissue and quantitated. Colonisation frequency was determined by the number of mice infected with *H. pylori* per group. Results are expressed as individual and average percent colonisation per group.

FIG. 7: *H. pylori* strains were tested in the C57BL/6 mouse model for colonisation of the stomach after 2 weeks. Mice (n=3) were challenged with $1\times10^9$ CFU/ml bacteria. Bacteria were cultured from mouse stomach tissue and quantitated. Colonisation frequency was determined by the number of mice infected with *H. pylori* per group. Results are expressed as individual and average percent colonisation per group.

FIG. 9: *H. pylori* strain genotype and clinical pathology.

DESCRIPTION OF THE PREFERRED EMBODIMENTS OF THE INVENTION

Figure 5:
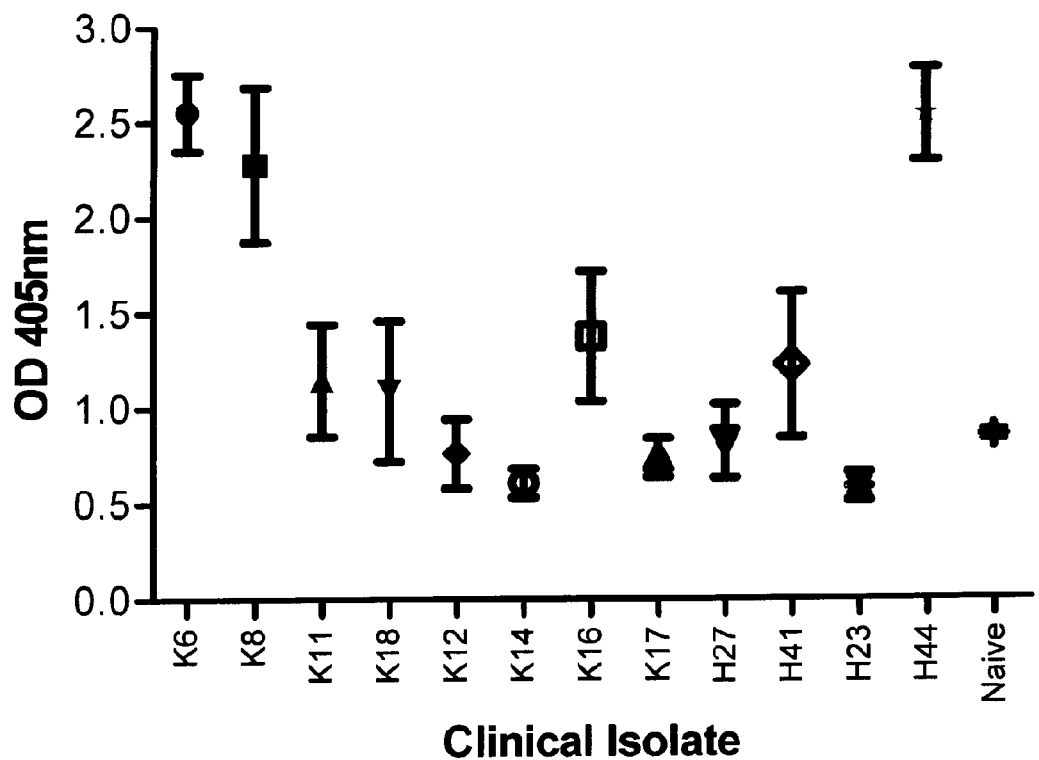
FIG. 5: Coloniser and non-coloniser *H. pylori* strains were used to challenge DBA/2 mice and measure *H. pylori* specific immune responses. Mice (n=5) were challenged with $1\times10^9$ CFU/ml bacteria. Three months later serum was collected and IgG specific antibodies measured by ELISA. Results are expressed as OD at 405 nm.

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional microbiological, immunological and molecular biological techniques and pharmacology within the skill of the art. Such techniques are well known to the skilled worker, and are explained fully in the literature. See, eg., Prescott et al. "Microbiology" (1999) 4$^{th}$ Edition, WCB McGraw-Hill; Sambrook et al., "Molecular Cloning: A Laboratory Manual" (1989) (2001), 2nd & 3rd Editions, Cold Spring Harbor Laboratory Press; and Roitt et al. "Immunology" (1998), 5th Edition, Mosby.

It must be noted that as used herein and in the appended claims, the singular forms "a", "an", and "the" include plural reference unless the context clearly dictates otherwise. Thus, for example, a reference to "a nucleic acid" includes a plurality of such nucleic acids, and a reference to "an isolated strain" is a reference to one or more strains, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein, the term "consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The present invention relates to *Helicobacter pylori* strains that are useful as live bacterial delivery vehicles. A key characteristic of these strains is their low pathogenicity. The term "low pathogenicity" refers to a *H. pylori* strain that is capable of establishing an infection that is asymptomatic, i.e. does not cause peptic ulcers or gastric cancer, and causes minimal pathology of the stomach mucosa, i.e. the presence of little or no atrophy, lymphocyte infiltration or granulocyte infiltration of the stomach epithelium.

In some embodiments, the *Helicobacter pylori* strains of the present invention do not express one or more functional virulence factors. The virulence factors, encoded by virulence genes, disrupt the mucosal barrier by damaging the epithelial cells and cause overt disease including peptic ulcers and gastric cancer. For example, the virulence gene vacA Si encodes a vacuolating cytotoxin, while the virulence gene cagA encodes toxin that is injected into the host cell via a type IV secretion. In a particular embodiment, the strains of the present invention lack either vacA s1 or cagA, i.e. do not express either functional vacA s1 or cagA. Without being bound by any particular hypothesis, it appears that both of these virulence factors are required for pathogenicity.

While it is important that bacterial delivery vehicles have low pathogenicity, it is also desirable that they form a chronic infection. The term "chronic infection" refers to an infection that is ongoing for 6 months or more. As such, in some embodiments, the *H. pylori* strains of the present invention will have the ability to form a chronic infection in a mammalian subject.

The term "mammalian subject" as used herein refers a human, a primate, an equine, a canine or a feline.

The *H. pylori* strains of the present invention also have the ability to naturally transform. The term "naturally transform", "natural transformation" and grammatical equivalents thereof, refers to the genetic alteration of a cell resulting from the uptake, genomic incorporation, and expression of exogenous DNA in laboratory conditions, without using conditions that do not normally occur in nature, e.g. electroporation. This characteristic facilitates the incorporation of a gene of interest, encoding a biologically active agent, into the genome of the bacteria and the production of a "recombinant strain".

The *H. pylori* strains of the present invention also have the ability to infect and colonise mice without prior host adaptation. Bacteria taken from humans will not necessarily infect a different species such a mouse. Therefore, host adaptation is often required before experimentation in a mouse model can begin. Mouse host adaptation generally involves passaging cells from mouse-to-mouse to yield host-adapted variants. Moreover, once experimentation has concluded in the mouse, the strain may not now infect and colonise humans, resulting in further manipulation being required. Accordingly, using strains of *H. pylori* isolated from humans that can infect mice without host adaptation limits manipulation to the *H. pylori* strain and allows direct translation of the strain to humans.

The inventors of the present invention have identified non-exclusive examples of clinical isolates of *H. pylori* having the desired characteristics of a bacterial delivery vehicle, as described above. The strains of *H. pylori* identified were deposited under terms in accordance with the Budapest Treaty with the National Measurement Institute (NMI), 1/153 Bertie Street, Port Melbourne, Victoria, Australia on Apr. 22, 2009 (OND737, OND738, OND739 and OND740) and May 28$^{th}$ 2010 (OND248 and OND256). The strains of *H. pylori* have been assigned the following accession numbers: V09/009,101 (OND737); V09/009,102 (OND738); V09/009,103 (OND739); V09/009,104 (OND740); V10/014,059 (OND248) and V10/014,060 (OND256).

The present invention also contemplates mutants or derivatives of *H. pylori* strains OND737, OND738, OND739, OND740, OND248 and OND256. The term "mutant" or "derivative" as used herein, refers to bacteria with genomic DNA at least about 80%, preferably at least about 90%, and most preferably at least about 95%, identical to that of *H. pylori* strains OND737, OND738, OND739, OND740, OND248 and OND256 and that have the corresponding characteristics of the strains, as described herein.

The *H. pylori* strains of the present invention may be used to deliver biologically active agents. Live bacterial delivery vehicles deliver biologically active agents by expressing a gene or genes encoding the biologically active agent. Generally, the gene of interest is encoded by a nucleic acid, which is preferably obtained in an isolated form. It will be appreciated by those skilled in the art that the isolated nucleic acid molecule of the present invention may be cDNA, genomic DNA, RNA, or a hybrid molecule thereof. Preferably, the isolated nucleic acid is cDNA.

The term "isolated nucleic acid", as used herein, is a nucleic acid, the structure of which is not identical to that of any naturally occurring nucleic acid or to that of any fragment of a naturally occurring genomic nucleic acid spanning more than three separate genes. The term therefore covers, for example, (a) a DNA molecule which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Methods for isolating nucleic acids are well known to those skilled in the art.

The isolated nucleic acid may be homologous or heterologous; however, generally the isolated nucleic acid will be heterologous, i.e., not expressed by *H. pylori* in nature or prior to introduction into the bacteria, or an ancestor thereof.

In some embodiments, the isolated nucleic acid encodes a biologically active agent. The skilled person will appreciate that the methods of the present invention could be used to deliver a range of biologically active agents. Examples of suitable agents include ones which are capable of functioning locally or systemically, e.g. an agent capable of exerting endocrine activities affecting local or whole-body metabolism and/or an agent which is capable of regulating the activities of cells belonging to the immuno/haemopoeitic system and/or an agent which is capable of affecting the viability, growth and differentiation of a variety of normal or neoplastic cells in the body or affecting the immune regulation or induction of acute phase inflammatory responses to injury and infection and/or an agent which is capable of enhancing or inducing resistance to infection of cells and tissues mediated by chemokines acting on their target cell receptors, or the proliferation of epithelial cells or the promotion of wound healing and/or an agent which modulates the expression or production of substances by cells in the body.

Specific examples of such biologically active agents include insulin, growth hormone, prolactin, calcitonin, luteinising hormone, parathyroid hormone, somatostatin, thyroid stimulating hormone, vasoactive intestinal polypeptide, a structural group 1 cytokine adopting an antiparallel 4 α helical bundle structure such as IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL or IFN α/β, a structural group 2 cytokine which are often cell-surface associated, form symmetric homotrimers and the subunits take up the conformation of β-jelly roll described for certain viral coat proteins such as the tumour necrosis factor (TNF) family of cytokines, eg TNF α, TNF β, CD40, CD27 or FAS ligands, the IL-1 family of cytokines, the fibroblast growth factor family, the platelet derived growth factors, transforming growth factor β and nerve growth factors, a structural group 3 cytokine comprising short chain α/β molecules, which are produced as large transmembrane pre-cursor molecules which each contain at least one epidermal growth factor (EGF) domain in the extracellular region, e.g., the EGF family of cytokines, the chemokines characterised by their possession of amino acid sequences grouped around conserved cysteine residues (the C-C or C-X-C chemokine subgroups) or the insulin related cytokines, a structural group 4 cytokine which exhibit mosaic structures such as the heregulins or neuregulins composed of different domains, e.g., EGF, immunoglobulin-like and kringle domains.

Alternatively, the biologically active agent can be a receptor or antagonist for a biologically active agent, as defined above.

Accordingly, the present invention provides a recombinant *H. pylori* strain expressing a biologically active agent for pharmaceutical use, e.g., for use in a method of treatment of the human or animal body and in particular prophylaxis ("vaccination").

The natural features of *H. pylori* infection such as the presence of specific, non-protective circulating antibodies and life-long persistence mean that *H. pylori* is particularly useful in delivering vaccine antigens and inducing an antibody response in an individual. Accordingly, in a particular embodiment, the present invention provides a recombinant strain of *H. pylori* expressing an antigen and a method of inducing an antibody response in an individual by administering that bacterium to an individual. An "antibody response" refers to the induction of specific antibodies against the antigen of interest expressed by the recombinant bacterium.

The isolated nucleic acid encoding the biologically active agent may be integrated into the genome of the *H. pylori* strain by any method known in the art. For example, an expression vector and/or vector plasmid may be employed to insert the gene of interest in the form of an isolated nucleic acid into the bacterial chromosome. In a preferred embodiment, the isolated nucleic acid will be incorporated into the bacterial chromosome by natural transformation and homologous recombination. For example, 0.3-2 µg DNA fragments containing an antibiotic marker or the mutated rpsL allele (Dailidiene et al. (2006) "Contraselectable streptomycin susceptibility determinant for genetic manipulation and analysis of *Helicobacter pylori*" Appl Environ Microbiol, 72, 5908-5914) in 5-15 µl of TE buffer is added to a *H. pylori* culture and mixed. The bacteria are then incubated for 24 hours in a gas chamber. DNA-treated cells are collected and plated onto selective blood agar plates supplemented with Kanamycin (10 µg/ml), Chloramphenicol (10 µg/ml), Streptomycin (10 ug/ml) and Erythromycin (10 µg/ml) and incubated. Growth of bacteria indicates that transformation was successful.

The present invention also provides a method of identifying a strain of *H. pylori* suitable for use as bacterial delivery vehicles. The first step of the method involves isolating a *H. pylori* strain from an individual asymptomatic for *H. pylori* infection. Preferably the individual will be at least 50 years of age, be asymptomatic for *H. pylori* infection and show no or little atrophy of the stomach epithelia. The isolated strain will then be tested to determine whether the strain has the ability to naturally transform and its ability to colonise mouse stomach mucosa without host adaptation. Isolated strains that are able to naturally transform and colonise mouse stomach mucosa without host adaptation will be designated suitable for use as bacterial delivery vehicles and for delivering biologically active agents in vivo.

The invention will now be further described by way of reference only to the following non-limiting examples. It should be understood, however, that the examples following are illustrative only, and should not be taken in any way as a restriction on the generality of the invention described above.

EXAMPLE 1

Isolation of Clinical Strains

Twenty three *H. pylori* clinical isolates were obtained from the Karolinska Institute, Sweden and 50 *H. pylori* clinical isolates from Sir Charles Gardiner Hospital, Western Australia. Clinical isolates were resurrected from glycerol stocks and grown on 6-antibiotic selective blood agar plates (Vancomycin 10 µg/ml, Trimethoprim Lactate µg/ml, Polymyxin B 2500 IU/L, Amphotericin B 2.5 µg/ml) in a gas-controlled chamber. After 24 hours of growth the bacteria were swabbed from the plate and re-suspended in BHIB (Oxoid). The bacteria were harvested directly from plates to give approximately $1 \times 10^9$ bacteria per ml by measuring optical density at 600 nm ($OD_{600}$). Genotyping of the strains was performed as described previously (Tiwari et al. (2007) "A simple multiplex PCR assay for diagnosing virulent *Helicobacter pylori* infection in human gastric biopsy specimens from subjects with gastric carcinoma and other gastro-duodenal diseases" J Appl Microbiol, 103, 2353-2360).

All clinical isolates were screened for their ability to take up DNA and integrate it into their genome by homologous recombination. *H. pylori* clinical isolates were inoculated from glycerol stock onto selective agar plates. Plates were incubated at 37° C. in a gas-controlled chamber containing two Campygen kit gas packs for 2-4 days. The bacteria were subcultured and re-plated onto fresh plates. Plates were further incubated in the chamber for 18-20 hours at 37° C. and single colonies were plated onto fresh plates supplemented with DENT (Oxoid, SR0147). Plates were incubated for 5 hours in the $CO_2$ incubator. Next, 0.3-2 µg DNA fragments containing an antibiotic marker or the mutated rpsL allele (Dailidiene et al. (2006) "Contraselectable streptomycin susceptibility determinant for genetic manipulation and analysis of *Helicobacter pylori*" Appl Environ Microbiol, 72, 5908-5914) in 5-15 µl of TE buffer was added to the *H. pylori* strains and mixed. Bacteria were incubated for a further 24 hours in the gas chamber. DNA-treated cells were collected and plated onto selective blood agar plates supplemented with Kanamycin (10 µg/ml), Chloramphenicol (10 µg/ml), Streptomycin (10 ug/ml) and Erythromycin (10 µg/ml) and incubated. Growth of bacteria was determined post-transformation.

FIG. 1 shows the frequency of strains that were able to undergo natural transformation and that became antibiotic resistant. Of the 73 strains screened, approximately 60% (42/73), 14 strains from the Karolinska (K) Institute and 28 strains from SCGH (H), were identified as being naturally transformable with DNA based on their antibiotic resistance phenotype. These strains were subsequently tested in vivo in the mouse model for their ability to colonise (Example 2).

EXAMPLE 2

Identification of Clinical Isolates that Colonise the Stomach in the *H. Pylori* DBA/2J Mouse Model The 42 clinical isolates identified in Example 1 (FIG. 1) were tested for their ability to colonise the stomach mucosa in the DBA/2J mouse model.

Female, 6-8 week old DBA/2J mice were purchased from the Animal Resources Centre, Australia. All mice were *H. pylori*-free and were allowed a 2 week acclimatisation period prior to the start of the experiment. Animals were provided acidified water and a standard (fishmeal-based) rodent diet ad libitum unless otherwise specified. In some experiments animals were fed vegetarian (fishmeal-free) or a semi-synthetic, casein-rich protein diets and neutral (non-acidic) drinking water. Food diets were sourced from Specialty Feeds, Western Australia. All experimental work is approved by the University of Western Australia Animal Ethics Committee under approval RA 3/100/676.

Mice (n=3) were challenged with $1 \times 10^9$ CFU/ml bacteria in BHIB. To determine the level of colonization, stomach tissue was harvested from animals either 4 or 24 weeks after challenge. Stomachs were dissected along the greater curvature and residual food removed by gently washing with PBS. Opened stomachs were placed in 500 µl PBS and homogenized with a 5 mm stainless steel bead for 30 seconds at a frequency of 30 (Qiagen TissueLyser II). Samples were further homogenized for 2 minutes at a frequency of 10. Serial dilutions of homogenates were plated on BHI agar plates supplemented with amphotericin B (8 µg/ml), trimethoprim (5 µg/ml) and vancomycin (6 µg/ml), nalidixic acid (10 µg/ml), polymyxin B (10 µg/ml) and bacitracin (200 µg/ml). Plates were placed in gas-controlled chambers containing two Campygen kit gas packs (Oxoid, CN0025A) and incubated at 37° C. Bacterial growth was determined 5-7 days post-plating.

Of the 42 strains identified to be naturally transformable, only 15 were able to successfully colonise in the DBA/2J *H. pylori* mouse model (FIG. 2). Preliminary results by original source are summarised in Table 1. The best colonising strains were identified and further validated for colonisation robustness and frequency of infection in vivo.

TABLE 1

SUMMARY OF TRANSFORMABLE, COLONISING *H. PYLORI* CLINICAL ISOLATES

| Source | Number | Transformable | Colonization | Total |
|---|---|---|---|---|
| Karolinska | 23 | 14/23 (60.8%) | 4/14 (28.5%) | 15 |
| SCGH | 50 | 28/50 (56%) | 11/28 (39%) | |

EXAMPLE 3

Robustness and Frequency of Infection

To further investigate the robustness of the 15 strains that colonised the mouse model in Example 2, more experiments with larger animal numbers were performed. This allowed for the selection of clinical isolates that were true colonisers. Multiple rounds of experimentation were done for each strain identified above to be naturally transformable and able to colonise the mouse stomach mucosa. Briefly, mice (n=10-12) were challenged with $1 \times 10^9$ CFU/ml bacteria. Four weeks later bacteria were cultured from mouse stomach tissue and quantitated.

The results demonstrated that 5 strains (K6, K8 K18, H27 and H40) identified in the preliminary in vivo screening were robust colonisers, while the remaining 10 strains were poor colonisers of the mouse gastric mucosa. Since SCGH clinical isolates were showing poor and inconsistent colonisation results, experiments were terminated after the second round (FIG. 3). SCGH strains also grew more slowly compared to strains sourced from the Karolinska Institute. These differences may be attributed to differences in culturing and storage techniques at individual locations.

EXAMPLE 4

Long Term Colonisation in the DBA/2J Mouse Model

The ability to establish chronic infection by *H. pylori* strains was addressed by performing a long term colonisation experiment. Based on the initial (Round 1) colonisation data, a selection of the strongest and poorest colonising clinical isolates were tested. Mice (n=4-6), as purchased and treated in Example 2, were orally challenged with $1\times10^9$ CFU/ml of colonising *H. pylori* strains (K6, K8, K11, K18, H27 and H41) and non-colonising strains (K12, K14, K16, K17, H23 and H44). Six months after oral challenge, bacteria were harvested and cultured from mouse stomach tissue and quantitated as described in the Examples above. Robust coloniser strains; K6, K8, K18 and H27 were still able to infect approximately 500 of animals (FIG. 4). As expected, mice infected with non-coloniser strains were not colonised and the weakly colonising strains K11 and H41 failed to colonise the stomach mucosa of mice long term. This indicates that different strains have different abilities to colonise the mouse stomach and here we have identified at least 4 strains that can do so without adaptation in the host.

EXAMPLE 5

Immunogenicity of Colonising *H. Pylori* Clinical Isolates

Next we determined the immunogenicity of the colonising *H. pylori* strains identified in the in vivo mouse model and compared them to non-colonising strains. *H. pylori* clinical isolates were tested for their ability to induce specific IgG antibody response 3 months after oral challenge in the DBA/2J mouse model. Mice (n=5) were orally challenged with $1\times10^9$ CFU/ml of colonising *H. pylori* strains (K6, K8, K11, K18, H27 and H41) and non-colonising strains (K12, K14, K16, K17, H23 and H44). Three months after infection, animals were bled, serum collected and *H. pylori*-specific IgG antibodies measured by ELISA.

96 well plates (Nunc Maxisorb®) were coated with 10 µg/ml *H. pylori* X47 cell lysate and incubated overnight at 4° C. Plates were then washed 5 times in PBS/0.05% Tween-20 and blocked with 2 BSA for 2 hours at 37° C. Plates were washed twice and serum samples (1/20 dilution) were added to the well in duplicate. The plates were then incubated for 1 hour at room temperature (RT), subsequently washed and detection antibody (anti-mouse IgG conjugated to alkaline phosphatase, 1/1000, Sigma) was added. Plates were further incubated for 1 hour at room temperature then washed. Plates were developed using p-NPP for 40 minutes before the reaction was stopped with 2M NaOH. Antibody titres were expressed as the optical density value measured at 405 nm.

The results showed that K6 and K8, two of the strongest coloniser strains, were the most immunogenic (FIG. 5). Clinical isolates, K11, K18, H27 and H41 were far less immunogenic. Interestingly, despite not being able to colonise the stomach mucosa 4 weeks after infection in the mouse model, clinical isolate H44 displayed a strong *H. pylori*-specific IgG response three months after oral challenge, suggesting that this strain could have transiently infected the mouse early during the course of the experiment.

Figure 6:
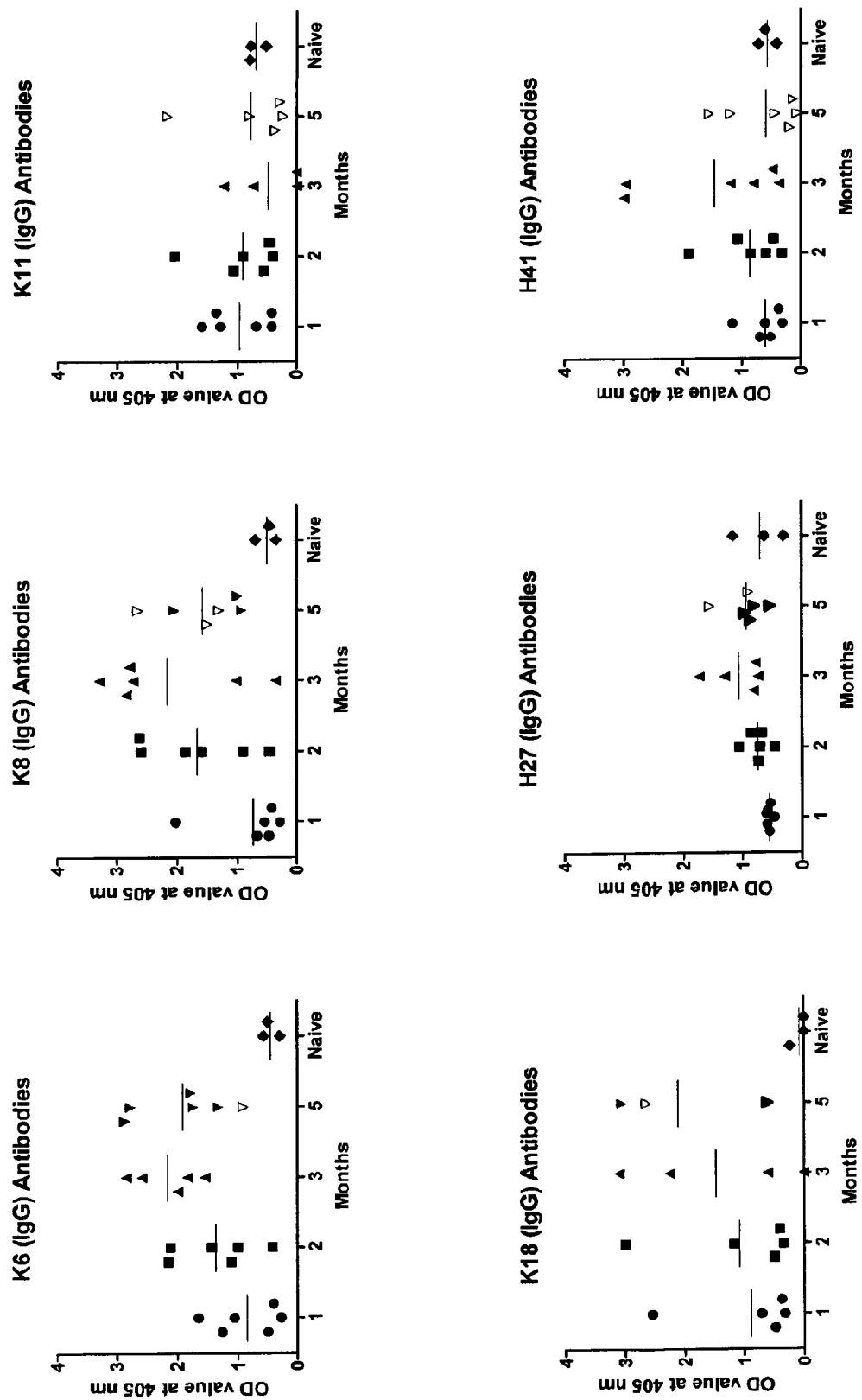
FIG. 6: Coloniser *H. pylori* strains were used to challenge DBA/2 mice and measure *H. pylori* specific immune responses. Mice (n=5) were challenged with $1\times10^9$ CFU/ml bacteria. Sera were collected at 1, 2, 3 and 5 months after challenge and IgG specific antibodies measured by ELISA. Results are expressed as OD at 405 nm.

In a further analysis, *H. pylori*-specific IgG antibodies were measured up to 5 months in mice challenged with colonising strains. Results demonstrated that K6 and K8 strains induced the strongest and most persistent *H. pylori*-specific antibody responses up to 5 months after challenge (FIG. 6). These data support the observation that K6 and K8 strains were the most immunogenic while K11, K18, H27 and H41 were less immunogenic.

EXAMPLE 6

Identification of Clinical Isolates that Colonise the Stomach in the *H. Pylori* C57BL/6 Mouse Model To ensure that candidate *H. pylori* strains were not missed in our screening in the DBA/2 mouse model (Example 2), we revisited screening in the C57BL/6 mouse model, which is far less permissive to infection by clinical isolates.

Female, 6-8 week old C57BL/6 mice were purchased from the Animal Resources Centre, Australia. All mice were *H. pylori-free* and were allowed a 2 week acclimatisation period prior to the start of the experiment. Animals were provided acidified water and a standard (fishmeal-based) rodent diet ad libitum unless otherwise specified. In some experiments animals were fed vegetarian (fishmeal-free) or a semi-synthetic, casein-rich protein diets and neutral (non-acidic) drinking water. Food diets were sourced from Specialty Feeds, Western Australia. All experimental work is approved by the University of Western Australia Animal Ethics Committee under approval RA 3/100/676.

The 14 transformable *H. pylori* strains identified in Example 1 were tested for colonization by the same procedure as used in Example 2. We identified an additional strain, K4 that successfully colonised in the C57BL/6 mouse model and a second strain, K12 was also detected albeit colonisation with this strain was far less robust (FIG. 7). The K8 strain was also picked up as a weak coloniser in this model. All remaining *H. pylori* clinical isolates failed to colonise C57BL/6 mice.

EXAMPLE 7

Optimization of the *H. Pylori* Mouse Model

Since the mouse model is not the natural host for *H. pylori* and establishing infection in this model can be difficult, we set out to optimise the mouse model by testing modifications to diet including food and water in order to improve colonisation of *H. pylori* strains in vivo.

First, we compared different food diets including the standard fishmeal-based diet, a vegetarian (non fishmeal) and a semi-synthetic casein-rich protein diet (93G). Second, we evaluated the effect of acidic (pH 2.5) versus neutral drinking water (pH 6). These approaches were tested to determine whether any would provide improvement in colonisation in the C57BL/6 and DBA/2 mouse model using the X47 lab strain.

Results showed improved colonisation by *H. pylori* in mice fed the casein-rich 93G diet (Specialty Feeds, Western Australia) when compared to the standard fishmeal diet (Table 2). The vegetarian (fishmeal free) diet did not show any improvement in colonisation (data not shown). The use of a semi-synthetic, casein-rich diet increased *H. pylori* colonisation rates in mice and thus resulted in an improved mouse model. Interestingly, altering the drinking water from standard acidified water (pH 2) to neutral water (pH 6) impacted negatively on the model with a decrease in the load of bacteria in the stomach (Table 2). In fact the use of acidic water was better for the mouse

TABLE 2

EFFECTS OF DIET ON COLONISATION OF *H. PYLORI* IN THE MOUSE MODEL

|  |  | Bacterial Load (CFU/ml/stomach) | |
|---|---|---|---|
|  |  | C57BL/6 | DBA/2 |
| Food | Standard | 1.1E+05 | 1.1E+04 |
| Water | 93G | 1.1E+06 | 4.1E+04 |
|  | Acid | 8.0E+04 |  |
|  | Neutral | 3.1E+03 |  |

*H. pylori* strain X47 was tested in the C57BL/6 and DBA/2 mouse model for colonisation of the stomach after 2-4 weeks. Mice (n=3) were challenged with $1 \times 10^9$ CFU/ml bacteria. Bacteria were cultured from mouse stomach tissue and quantitated. Colonisation load per mL of stomach tissue was determined for each animal. Results are expressed as average bacterial load per group. model most likely due to the suppression of other bacteria present in the stomach of mice. Subsequent in vivo screening experiments were performed under these dietary conditions.

EXAMPLE 8

Screening of *H. Pylori* Colonising Strains in Additional Mouse Models

Since each *H. pylori* clinical isolate has unique properties and is characteristically different, it was possible that other mouse strains, differing in their genetic background, would be more suitable as an in vivo model. Hence, we screened 5 previously identified *H. pylori* strains (K4, K8, K12, K11 and K18) in 6 mouse strains including C3H, FVB/n, CBA, DBA/2, 129/s and Swiss (ARC) for colonisation.

Female, 6-8 week old DBA/2J, C3H, CBA, FVB/n, 129/s, Swiss (ARC) and C57BL/6 mice were purchased from the Animal Resources Centre, Australia. All mice were *H. pylori*-free and were allowed a 2 week acclimatisation period prior to the start of the experiment. Animals were provided acidified water and a standard (fishmeal-based) rodent diet ad libitum unless otherwise specified. In some experiments animals were fed vegetarian (fishmeal-free) or a semi-synthetic, casein-rich protein diets and neutral (non-acidic) drinking water. Food diets were sourced from Specialty Feeds, Western Australia. All experimental work is approved by the University of Western Australia Animal Ethics Committee under approval RA 3/100/676.

Due to culturing difficulties, the K6 strain was not included in the experiment. In addition, the mouse-adapted strain X47 was included as a comparator and all experiments were performed using mice fed the semi-synthetic casein-rich protein diet (93G diet) and acidified water.

Figure 8:
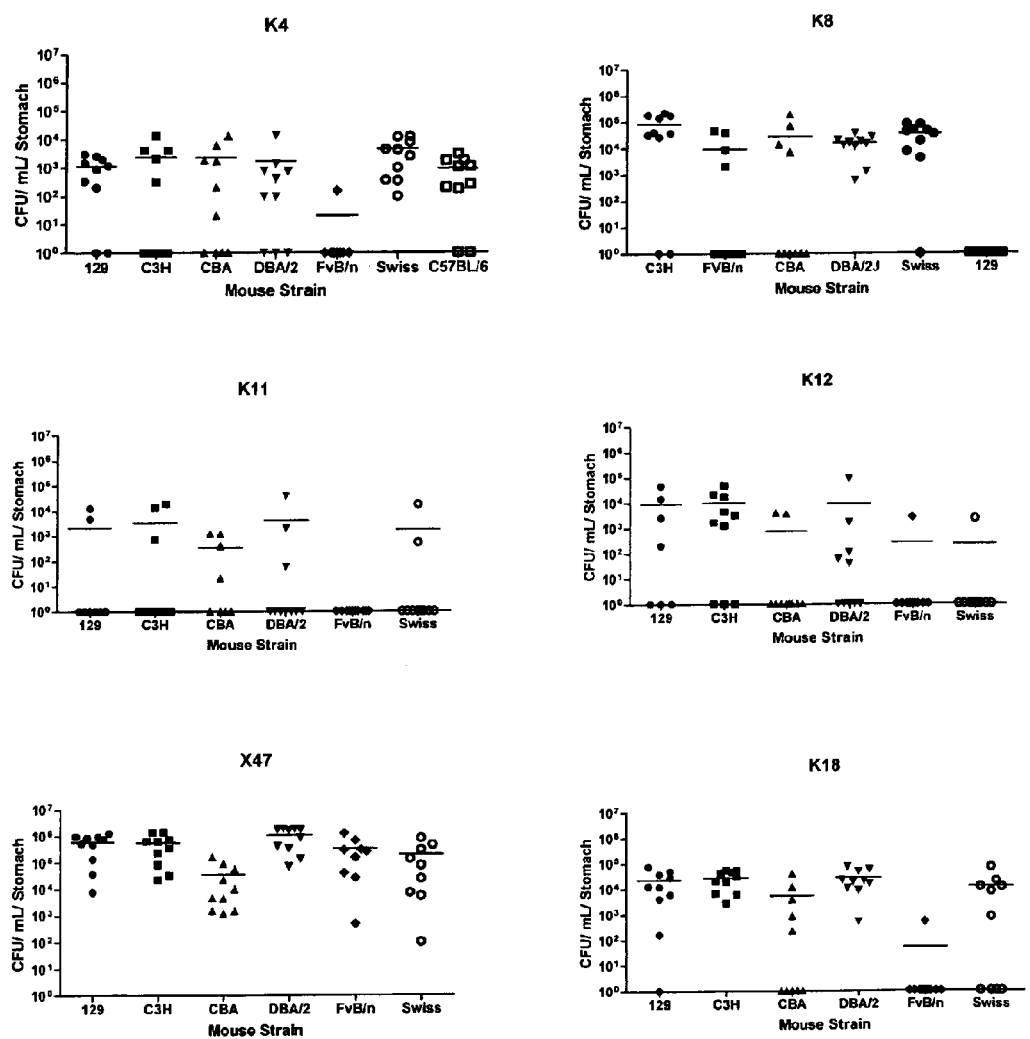
FIG. 8: *H. pylori* strains were tested in the various mouse strains for colonisation of the stomach 4 weeks after oral infection. Mice (n=10) were challenged with $1\times10^9$ CFU/ml bacteria. Bacteria were cultured from mouse stomach tissue and quantitated. Colonisation frequency was determined by the number of mice infected with *H. pylori* per group.

Results showed that K4, K8 and K18 strains were able to colonise almost all mouse strains well and to a high degree. K11 and K12 strains were able to colonise the various mice albeit at a much lower frequency. As expected, X47 was able to colonise all mouse strains robustly and with a high level of bacterial load. These results are depicted below in Table 3 and in FIG. 8.

Taken together, K4, K8 and K18 were considered broad-spectrum, robust colonisers of mice and performed the best in the various mouse models whereas K11 and K12 were poorer colonisers of mice.

TABLE 3

COLONISATION RATE OF *H. PYLORI* CLINICAL STRAINS IN VARIOUS MOUSE STRAINS

| | Mouse Strains (# mice colonised, n = 10) | | | | | |
|---|---|---|---|---|---|---|
| Strains | 129/s | C3H | CBA | DBA/2 | FVB/n | Swiss |
| K4 | 8/10 | 5/10 | 6/10 | 7/10 | 1/10 | 10/10 |
| K8 | 0/10 | 8/10 | 4/10 | 10/10 | 4/10 | 9/10 |
| K11 | 2/10 | 3/10 | 4/10 | 3/10 | 0/10 | 2/10 |
| K12 | 4/10 | 7/10 | 2/10 | 5/10 | 1/10 | 1/10 |
| K18 | 9/10 | 10/10 | 5/10 | 10/10 | 1/10 | 6/10 |
| X47 | 10/10 | 10/10 | 10/10 | 10/10 | 10/10 | 10/10 |

*H. pylori* strains were tested in the various mouse strains for colonisation of the stomach 4 weeks after oral infection. Mice (n=10) were challenged with $1 \times 10^9$ CFU/ml bacteria. Bacteria were cultured from mouse stomach tissue and quantitated. Colonisation frequency was determined by the number of mice infected with *H. pylori* per group.

EXAMPLE 9

Screening of *H. Pylori* Colonising Strains in the Gerbil Model

To validate whether the 6 identified *H. pylori* strains (K4, K6, K8, K12, K11 and K18) were robust and broad colonisers they were screened in the gerbil model. The gerbil model is a more relevant model of *H. pylori* infection as it closely mimics the pathology (gastritis) observed in human infection.

Briefly, animals at the age of 8-12 weeks were challenged orally three times over five consecutive days with approximately $1 \times 10^9$ viable *H. pylori* (individual strains or pools of 5 strains) grown on agar plates (GC agar, Oxoid, Germany) supplemented with horse serum (8%), vancomycin (10 mg/l), trimethoprim (5 mg/l), nystatin (1 mg/l). The animals were sacrificed after 3-5 weeks of infection, the stomach opened along the greater curvature and the gastric tissue conserved separately as antrum and corpus. Each antral and corpus tissue specimen was homogenized in 1 ml *Brucella* broth and appropriate dilutions were spread on selective serum plates (GC agar, see above) and incubated under micro-aerophilic conditions (85% $N_2$, 10% $CO_2$, 5% $O_2$) at 37° C. for up to five days. Numbers of colony forming units (CFU) were expressed per gram of gastric tissue.

In the initial screening all 4 strains (challenged individually) failed to colonise the gerbil gastric mucosa. Subsequently, a second screening to test the remaining 10 transformable K strains was performed. Gerbils were challenged with a mixture of 5 strains and colonising strains were cultured from gastric biopsies and identified by genotyping fingerprinting. Interestingly, two strains, K4 and K12, were able to colonise the gerbil host (FIG. 9) and both strains were not identified in the original screening in the DBA/2 mouse model.

Furthermore after extensive screening in the mouse, the K4 strain was shown to be a good, robust coloniser of both the mouse and gerbil models. These data reflect the diversity of *H. pylori* strains and the difficulties in using human clinical isolates in preclinical animal models.

EXAMPLE 10

Screening of *H. Pylori* Colonising Strains in the Monkey Model

Non-human primates (monkeys) are considered to be closely related to humans and as a result are a relevant model of human disease, including *H. pylori* infection. Here we set out to validate previously identified *H. pylori* strains in the monkey model.

Adult (>5 years old) cynomolgus monkeys obtained from Valley Biosystems (West Sacramento, Calif.) were first screened for *H. pylori* infection using serology that is 95% sensitive and 94% specific in monkeys (Solnick et al. (2001), Infect. Immun. 69:6887-6892). Sero-negative monkeys also underwent endoscopy and those with negative cultures and histology for *H. pylori* were transferred to the California National Primate Research Center in Davis to be used in *H. pylori* challenge experiments. We estimate that approximately 25% of animals will be sero-negative and that 75% of these will be negative on gastric biopsy.

Monkeys not infected with *H. pylori* were randomly assigned to receive *H. pylori* challenge or control. A mixture of *H. pylori* strains K6 (OND737), K8 (OND738) and K11 (OND739) were used for the challenge. Due to culturing difficulties OND740 was not used in this experiment. Approximately $1 \times 10^9$ viable *H. pylori* were inoculated by oral gavage in monkeys sedated with ketamine (10 mg/kg IM). Gastric biopsies were taken one month after challenge to confirm *H. pylori* infection. CFU were quantitated as previously described.

Two strains, K6 and K11 successfully colonised the monkey stomach (FIG. 9).

EXAMPLE 11

Clinical and Genotypic Characteristics of the Strains

The clinical and histological data of the four selected mouse-colonising strains and the 2 gerbil-colonising strains (K4, K12) are summarised in FIG. 9. The six selected strains were designated OND737, OND738, OND739, OND740, OND248 and OND256, respectively (Table 4).

TABLE 4

NOMENCLATURE OF *H. PYLORI* STRAINS

| Strain | OND# |
| --- | --- |
| K1 | 245 |
| K4 | 248 |
| K6 | 737 |
| K8 | 738 |
| K9 | 253 |
| K10 | 254 |
| K11 | 739 |
| K12 | 256 |
| K14 | 258 |
| K16 | 260 |
| K17 | 261 |
| K18 | 740 |
| K19 | 263 |
| K21 | 265 |

Reference for nomenclature system for *H. pylori* clinical isolates. Each transformable K strain has been allocated a unique OND number.

All strains originated from asymptomatic patients over 52 years of age. Upon endoscopy little or no atrophy of the stomach epithelium could be observed and only the K18 (OND740) strain displayed a higher grade of granulocyte infiltration. The genotype of the strains was tested by multiplex PCR for the presence of the vacA s1, vacA s2, cagA, cagT, cagPAI and hrgA alleles. Interestingly, the strains were either vacA s1 or cagA negative (K6) or vacA s2 and cagA positive suggesting that the presence of the vacAs1 allele and cagA is exclusive in asymptomatic patients.

The results demonstrate that human clinical isolates of *H. pylori* can vary significantly in their pathogenicity, immunogenicity and virulence. Here we have shown that *H. pylori* strains also vary in their ability to take up DNA and integrate it into their genome by homologous recombination, colonise the mouse stomach and induce specific antibodies. This study has identified six *H. pylori* strains that, without adaptation in the host, are robust colonisers in a *H. pylori* animal model.

Furthermore, two of the identified strains induced high titres of specific antibodies and one strain was a robust coloniser in both models. Taken together, this study has identified multiple *H. pylori* strains that would be suitable for use as bacterial delivery vehicles based on their isolation from asymptomatic elderly patients, low grade clinical pathology of the stomach, genetic manipulation, ability to colonise the stomach in an animal model and the capacity to elicit a strong immune response.

EXAMPLE 12

Immunoblot Analysis of *H. Pylori* Clinical Isolates

In order to determine whether *H. pylori* strains differ in their immunogenic profile, immunoblot analysis was done to identify protein patterns of the selected *H. pylori* clinical isolates (K6, K8, K11, K18 and H41) using sera obtained in the DBA/2 mouse model. Immunoblots against whole cell lysate and outer and inner membrane proteins were compared for each respective *H. pylori* strain. X47 was used included as a benchmark as this strain is known to be immunogenic in mice.

Harvested bacteria from plate cultures were diluted to a concentration of 10 $OD_{600}$ nm units in 400 µl of 1×PBS and sonicated twice for 30 seconds. After sonication, the bacterial suspension was denatured in 100 µl 5× sample buffer for SDS-PAGE by heating to 95 degrees for 5 minutes and cooling to room temperature.

Alternatively bacteria were harvested and the outer membrane proteins were extracted by glycine extraction. Cell pellets equivalent to 10 $OD_{600}$ nm units were resuspended in 200 µl glycine buffer (pH 2.2) and incubated for 5 min at RT. Cells were then centrifuged (2 minutes, 14000 rpm, room temperature). The supernatants were mixed with 30 µl Tris (pH10.8) to neutralize the protein fractions. The pellets of the glycine extraction were resuspended in 400 µl 1×PBS, sonificated and denatured in 5× sample buffer for SDS-PAGE as described above.

The samples (10 µl in each lane) were electrophoresed on SDS polyacrylamide mini gels using a MiniPROTEAN® Tetra Cell electrophorese unit (Biorad) using a 4% stacking gel and a 10% separating gel. Separated antigens were transferred to a polyvinylidene difluoride membrane (0.45 µM; IMMOBILON-P®; Millipore) using an electroblotting apparatus (TRANS-BLOT® SD Semi-Dry Transfer Cell; Biorad). Membranes were blocked overnight at 4° C. with 5% non-fat dry milk in 1×TBS+0.2% polyoxyethylene (20) sorbitan monolaurate (TWEEN20™).

Membranes were incubated with serum from mice infected with the respective *H. pylori* strains (diluted 1:50 in 1×TBS+

0.1% polyoxyethylene (20) sorbitan monolaurate (TWEEN20™) for 1 hour at room temperature. Membranes were washed three times with 1×TBS+0.1% Tween20 and then incubated with a 1:5000 dilution of horse radish peroxidase (HRP)-conjugated goat anti-mouse IgG FCγ (Jackson Immunoresearch) diluted in 1×TBS+0.1% polyoxyethylene (20) sorbitan monolaurate (TWEEN20™) for 1 hour at room temperature. Membranes were washed with 1×TBS+0.1% polyoxyethylene (20) sorbitan monolaurate (TWEEN20™) as described above and incubated with chemiluminescent peroxidase substrate solution (CHEMILUMINESCENT PEROXIDASE SUBSTRATE-3™, Sigma). Membranes were evaluated for banding patterns with the FujiFilm LAS-3000 Imager.

Figure 10:
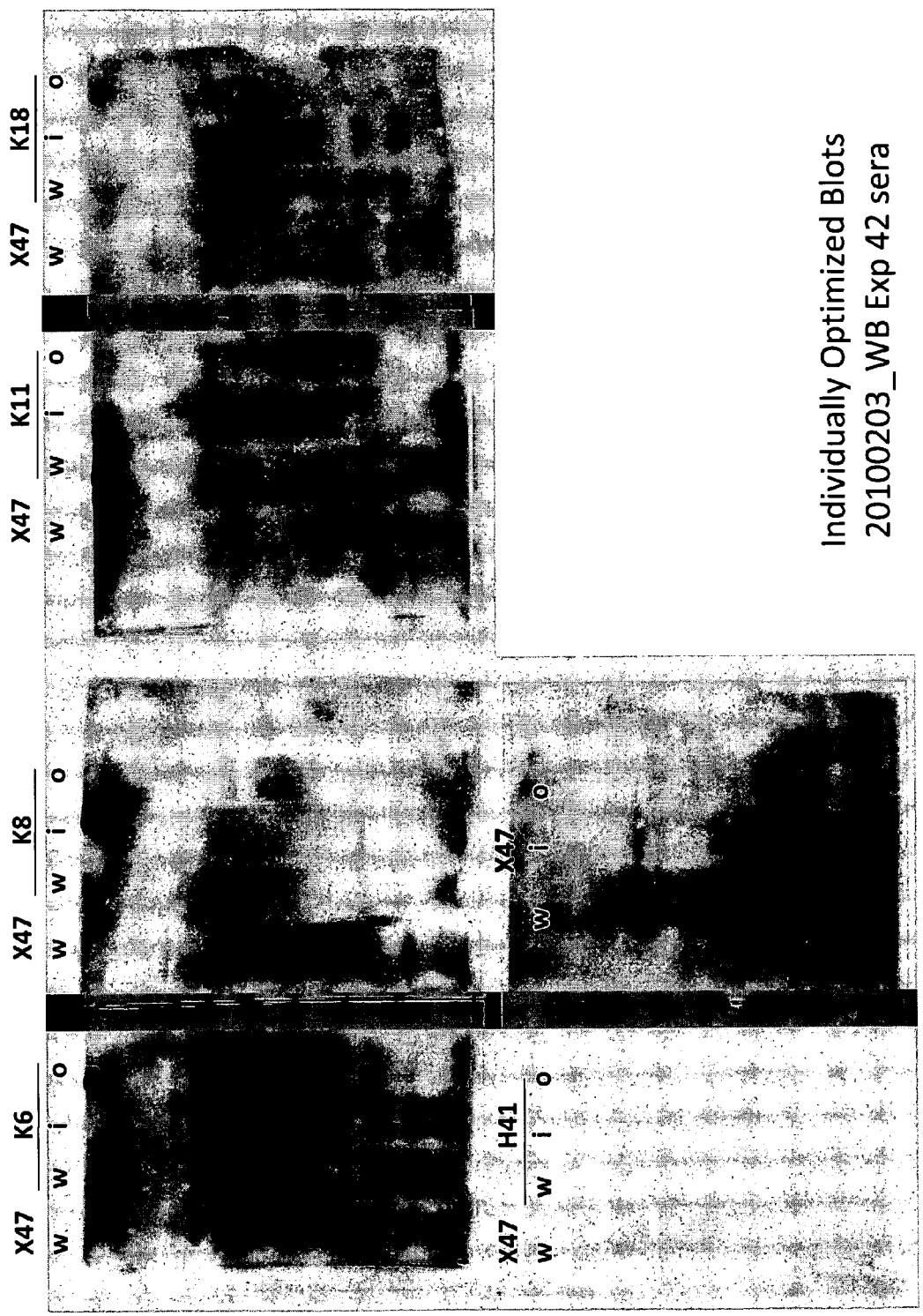
FIG. 10: Immunoblots using pooled sera from DBA/2 mice orally challenged with *H. pylori* strains after 3 months. Mice (n=5) were challenged with $1\times10^9$ CFU/ml bacteria. Sera were collected and pooled for immunoblot analysis against bacterial whole cell lysate (w) and outer (o) and inner (i) membrane proteins.

Results demonstrated that for each bacterial strain there was a general pattern of immunogenic proteins with slightly variations in pattern profiles. K6, K8 and K18 strains showed a more intense banding pattern suggesting that these strains may be more immunogenic in vivo (FIG. 10), which would be consistent with serology data previously described.

EXAMPLE 13

Genetic Fingerprinting of *H. Pylori* Clinical Isolates

Genetic fingerprinting can be used to estimate the genetic variability in bacterial populations. These fingerprints provide unique identification patterns for each strain. Genetic fingerprints for the 14 transformable K strains were produced to be able to identify output bacterial isolates in experimental conditions where the host has been challenged with a mixture of several strains. The RAPD PCR assay allows for a unique genetic pattern to decipher each *H. pylori* strain.

Bacterial strains were cultured on Columbia blood agar plates in a microaerophilic atmosphere for 48 at 37° C. Bacterial cell mass from approximately half of an agar plate with confluent growth was carefully harvested into 0.85% sodium chloride solution and centrifuged at 4000 g for 8 min. The supernatant was discarded and the pellet was suspended in 180 µl digestion buffer and 20 µl proteinase K. Samples were incubated for 4-12 hours at 55° C. with occasional vortexing and genomic DNA was then purified using a PURELINK® Genomic DNA mini kit from Invitrogen according to instructions.

RAPD was performed as described by Akopyanz et al. (1992), *Nucl. Acids Res.*, 20:5137-5142.

Primers 1254 and 1281 were used. A primer was always used separately in the PCR reaction.

```
                                             SEQ ID NO: 1
    1254    (5'-CCGCAGCCAA-3')
                                             SEQ ID NO: 2
    1281    (5'-AACGCGCAAC-3')
```

PCR reaction (50 µl volume) final concentration:

| | |
|---|---|
| Buffer | 100 mM Tris-HCl, 500 mM KCl, pH 8.3 |
| dNTPs | 250 µM of each |
| Primer | 0.8 µM of either 1254 or 1281 |
| MgCl$_2$ | 3 mM |
| BSA | 0.01% (w/v) |
| Template | 10-100 ng DNA (generally 5 µl of the extracted gDNA sample) |
| Taq | 2 units (recombinant Taq polymerase from Roche) |

Amplification Cycle:
4 cycles of [94° C., 5 min; 36° C., 5 min; and 72° C., 5 min]
30 cycles of [94° C., 1 min; 36° C., 1 min; and 72° C., 2 min]
72° C. for 10 min Gel electrophoresis: 10-15 µl of the PCR product was separated through a 1.5% (w/v) agarose gel at 90 V for 1 hour.

Figure 11:
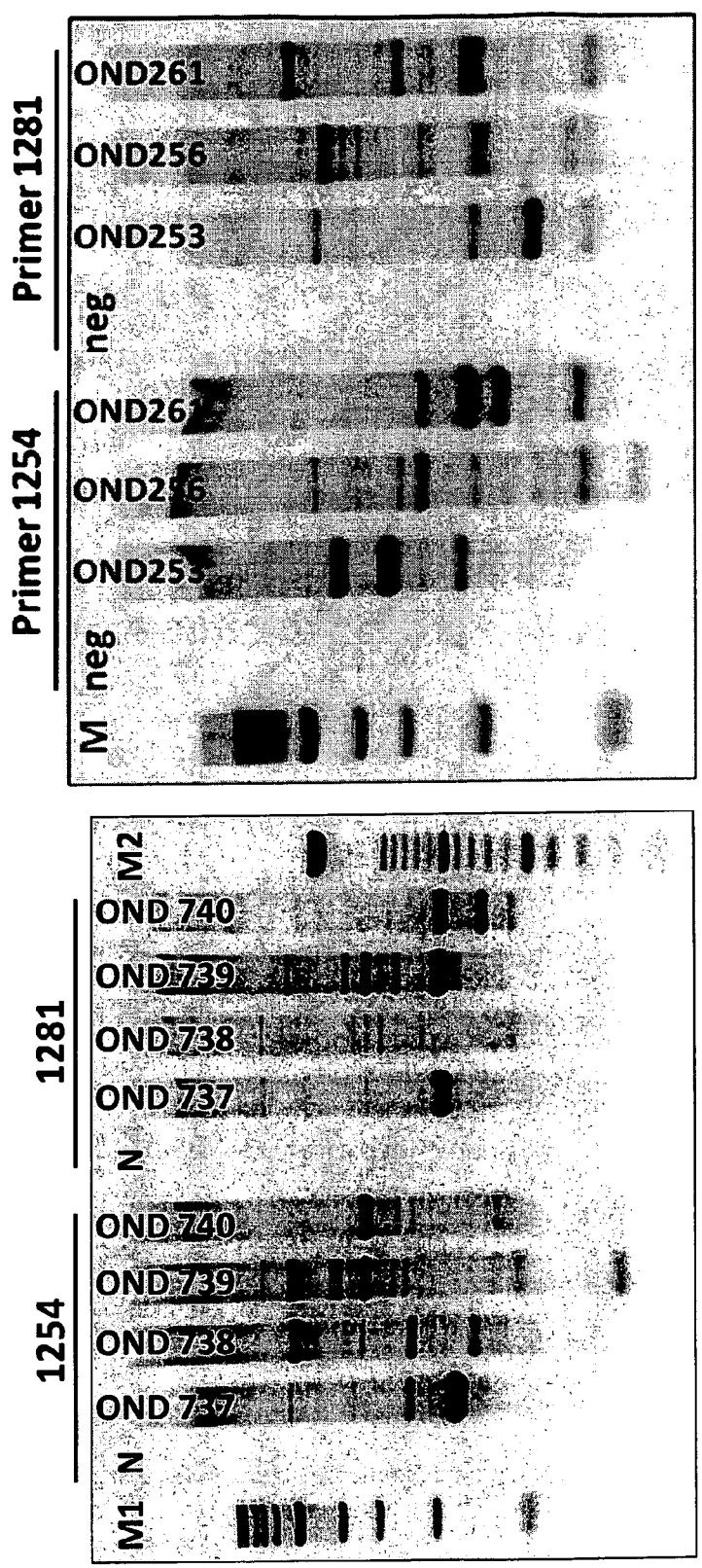
FIG. 11: RAPD PCR of *H. pylori* strains amplified with primer 1254 or 1281. Lane M or M1: 1 kb DNA ladder, lanes N: negative controls for each of the primer, OND lanes: individual *H. pylori* strains respectively, lane M2, 100 bp DNA ladder. See Table 10 for nomenclature reference.

As expected, unique banding patterns of the arbitrarily amplified genomic DNA samples of the 14 individual K strains were obtained with both of the primers (FIG. 11). For certain strains, one or the other primer produced a more characteristic banding pattern. OND258 (K14) and OND253 (K9) are most similar and might represent a familial strain. Table 4 summarises the nomenclature of the *H. pylori* strains with reference to the OND identification number.

The invention claimed is:
1. An isolated strain of *H. pylori* comprising the following characteristics: (a) low pathogenicity; (b) ability to naturally transform; and (c) ability to colonize mouse stomach mucosa without host adaptation, wherein said *H. pylori* is selected from the group consisting of OND737, as deposited in the National Measurement Institute under Accession No. V09/009101; OND738, as deposited in the National Measurement Institute under Accession No. V09/009102; OND739, as deposited in the National Measurement Institute under Accession No. V09/009103; OND248, as deposited in the National Measurement Institute under Accession No. V10/014059; OND256 as deposited in the National Measurement Institute under Accession No. V10/014060 and OND740, as deposited in the National Measurement Institute under Accession No. V09/009104.

2. The isolated strain of *H. pylori* of claim 1, wherein the *H. pylori* is strain OND737, as deposited in the National Measurement Institute under Accession No. V09/009101.

3. The isolated strain of *H. pylori* of claim 1, wherein the *H. pylori* is strain OND738, as deposited in the National Measurement Institute under Accession No. V09/009102.

4. The isolated strain of *H. pylori* of claim 1, wherein the *H. pylori* is strain OND739, as deposited in the National Measurement Institute under Accession No. V09/009103.

5. The isolated strain of *H. pylori* of claim 1, wherein the *H. pylori* is strain OND740, as deposited in the National Measurement Institute under Accession No. V09/009104.

6. The isolated strain of *H. pylori* of claim 1, wherein the *H. pylori* is strain OND248, as deposited in the National Measurement Institute under Accession No. V10/014059.

7. The isolated strain of *H. pylori* of claim 1, wherein the *H. pylori* is strain OND256, as deposited in the National Measurement Institute under Accession No. V10/014060.

8. The isolated *H. pylori* strain of claim 1, which is transformed with a gene of interest encoded by a nucleic acid molecule.

9. The isolated *H. pylori* strain of claim 8, wherein the nucleic acid molecule is integrated into the genome of the *H. pylori* strain.

10. The isolated *H. pylori* strain according to claim 8, wherein the nucleic acid encodes a polypeptide homologous to *H. pylori*.

11. The isolated *H. pylori* strain of claim 8, wherein the nucleic acid encodes a polypeptide heterologous to *H. pylori*.

12. A method of inducing an antibody response in a mammalian subject comprising the step of administering to the mammalian subject the strain of *H. pylori* of claim 1.

* * * * *